United States Patent
Daniels et al.

(10) Patent No.: US 6,958,142 B2
(45) Date of Patent: Oct. 25, 2005

(54) NASAL SPRAY FORMULATION AND METHOD

(75) Inventors: John R. Daniels, Pacific Palisades, CA (US); Malcolm C. Pike, Marina Del Rey, CA (US); Darcy V. Spicer, La Canada, CA (US); AnnaMarie Daniels, Pacific Palisades, CA (US)

(73) Assignee: Balance Pharmaceuticals, Inc., Santa Monica, CA (US)

( * ) Notice: Subject to any disclaimer, the term of this patent is extended or adjusted under 35 U.S.C. 154(b) by 179 days.

(21) Appl. No.: 10/298,378

(22) Filed: Nov. 15, 2002

(65) Prior Publication Data

US 2004/0022739 A1 Feb. 5, 2004

Related U.S. Application Data

(60) Provisional application No. 60/400,575, filed on Aug. 2, 2002.

(51) Int. Cl.$^7$ .......................... A61K 9/12; A61K 31/56; A61F 2/02
(52) U.S. Cl. .................. 424/45; 424/434; 424/426; 424/239; 514/2; 514/58; 514/874
(58) Field of Search .................... 424/45, 434, 426, 424/239; 514/2, 58, 874, 841, 843

(56) References Cited

U.S. PATENT DOCUMENTS

| | | |
|---|---|---|
| 4,315,925 A | 2/1982 | Hussain et al. |
| 4,383,993 A | 5/1983 | Hussain et al. |
| 4,476,116 A | 10/1984 | Anik |
| 4,596,795 A | 6/1986 | Pitha |
| 4,659,696 A | 4/1987 | Hirai et al. |
| 4,724,064 A | 2/1988 | Reid |
| 5,089,482 A | 2/1992 | Hermens et al. |
| 5,116,817 A | 5/1992 | Anik |
| 5,130,137 A | 7/1992 | Crowley, Jr. |
| 5,211,952 A | 5/1993 | Spicer et al. |
| 5,296,468 A | 3/1994 | Hoeger et al. |
| 5,340,584 A | 8/1994 | Spicer et al. |
| 5,340,585 A | 8/1994 | Pike et al. |
| 5,340,586 A | 8/1994 | Pike et al. |
| 5,681,817 A | 10/1997 | Hodgen et al. |
| 5,955,454 A | 9/1999 | Merkus |
| 5,977,070 A | 11/1999 | Piazza et al. |
| 6,225,298 B1 | 5/2001 | Spicer et al. |
| 2001/0016578 A1 | 8/2001 | Spicer et al. |

FOREIGN PATENT DOCUMENTS

| | | |
|---|---|---|
| EP | 0 709 099 A2 | 5/1996 |
| EP | 0 538 443 B1 | 10/1997 |
| WO | WO 92/01440 | 2/1992 |
| WO | WO 92/18107 | 10/1992 |
| WO | WO 94/26207 | 11/1994 |
| WO | WO 94/26208 | 11/1994 |
| WO | WO 96/15794 | 5/1996 |

OTHER PUBLICATIONS

Hermens, W., et al., *Pharmaceutical Research* 7(5):500–503, (1990).
Hermens, W., *Pharmaceutisch Weekblad Scientific Edition* 14(4A):253–257, (1992).
Sugimoto, A.K., et al., *Fetrility and Sterility* 60(4):672–674, (1993).

*Primary Examiner*—Gary Kunz
*Assistant Examiner*—Mina Haghighatian
(74) *Attorney, Agent, or Firm*—Judy M. Mohr; Perkins Coie LLP

(57) ABSTRACT

A nasal spray formulation for use in female contraception or in the treatment of benign gynecological disorders is described. The nasal preparation is comprised of a GnRH compound and an estrogenic compound in the form of a water-soluble complex with a water-soluble cyclodextrin. The preparation effectively suppresses ovarian estrogen and progesterone production, and prevents signs and symptoms of estrogen deficiency, without a significant increase in the risk of endometrial hyperplasia.

18 Claims, 3 Drawing Sheets

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 10
<223> OTHER INFORMATION: amino acid linked to NH2

<400> SEQUENCE: 1

Glu His Trp Ser Tyr Gly Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Xaa = Any Amino Acid in D configuration

```
-continued

<220> FEATURE:
<221> NAME/KEY: VARIANT
<222> LOCATION: 10
<223> OTHER INFORMATION: Amino Acid linked to NH2

<400> SEQUENCE: 2

Glu His Trp Ser Tyr Xaa Leu Arg Pro Gly
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Amino Acid in D configuration
<220> FEATURE:
<221> NAME/KEY: VARIANT
<222> LOCATION: 9
<223> OTHER INFORMATION: Amino Acid linked to ethylamide

<400> SEQUENCE: 3

Pro His Trp Ser Tyr Trp Leu Arg Pro
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Amino Acid in D configuration
<220> FEATURE:
<221> NAME/KEY: VARIANT
<222> LOCATION: 10
<223> OTHER INFORMATION: Amino Acid linked to NH2

<400> SEQUENCE: 4

Glu His Trp Ser Tyr Ala Leu Arg Pro Gly
1               5                   10
```

NASAL SPRAY FORMULATION AND METHOD

This application claims the benefit of U.S. Provisional Application No. 60/400,575, filed Aug. 2, 2002, incorporated herein by reference in its entirety.

FIELD OF THE INVENTION

The present invention relates to compositions comprising a gonadotropin releasing hormone compound and an estrogenic compound for mucosal delivery, particularly nasal delivery, for contraception and/or treatment of benign gynecological disorders. The invention also relates to methods for preparing the compositions and to methods of treatment using such compositions.

BACKGROUND OF THE INVENTION

During a woman's reproductive life, a delicate and complex interplay of hormones are timed and controlled by the hypothalamus. The hormones that participate in the feedback system regulating the menstrual cycle include estrogens and progesterone, the pituitary gonadotropins FSH (follicle stimulating hormone) and LH (luteinizing hormone), and gonadotropin-releasing hormone (GnRH) from the hypothalamus.

Manipulation of the hormonal balance is a recognized approach of contraception and of treatment of benign gynecological disorders. In particular, administration of a GnRH compound for contraception has been described (U.S. Pat. Nos. 5,340,584; 5,211,952). Typically, the GnRH compound is administered in a slow or controlled-release fashion for continuous suppression of ovarian estrogen and progesterone production. Estrogen, often a progestin, and sometimes an androgen, are "added-back" to ameliorate the effects of hormonal deficiency. The hormone add-backs are also often administered in a slow, controlled-release or time-release fashion to maintain a constant hormonal serum level.

Treatment of benign gynecological disorders by administration of a GnRH compound has also been described (U.S. Pat. Nos. 5,340,584; 5,340,585; 5,681,817). During a women's reproductive years, defined as the time between onset of menses (menarche) and the final episode of bleeding (menopause), that is a premenopausal woman, a variety of benign gynecological disorders can occur. Common benign gynecological disorders include, but are not limited to, premenstrual syndrome, endometriosis, uterine leiomyomata (uterine fibroids), and polycystic ovarian syndrome. As for contraceptive use, a GnRH compound is administered to suppress ovarian follicle development and sex steroid production to relieve or treat symptoms associated with the disorder.

The administration of drugs by absorption through mucosae, such as the nasal mucosa or vaginal mucosa, has been of considerable interest in recent years. This route of drug delivery is an alternative to oral administration in cases where drugs are poorly absorbed or are extensively metabolized in the gastrointestinal tract or subjected to first-pass metabolism in the liver. In particular, nasal mucosa has the desirable properties of being highly vascular leading to rapid uptake and the avoidance of first-pass metabolism in the liver, since the venous system from the nose passes directly into the systemic circulatory system. The nasal mucosa also exhibits moderate permeability to water-soluble compounds, comparable to that of the ileum. The permeability of nasal mucosa is higher for most compounds than other mucosae, due in part to the difference in structure of the cells lining the body cavities.

Efficiency of delivery of drugs by an intra-nasal route is influenced by the degree and rapidity of enzymatic degradation, the nasal clearance rate, as well as the drug's permeability through the mucosa. The clearance rate is produced by the coordinated movement of cilia and is known to be highly dependent upon the prevailing physiological and pathological conditions. Thus, for many drugs administration intranasally is inefficient due to low uptake of the drug, hence low bio-availability.

Another potential problem associated with intranasal delivery is mucosal irritation. Irritation caused by the drug itself and/or by absorption or penetration promoters or enhancers often limits the success of nasal formulations. Chronic administration of irritating nasal formulations can cause necrosis, inflammation, exudation, removal of the epithelial monolayer or can lead to irreversible damage to the nasal mucosa.

Nasal formulations comprised of a GnRH compound have been described (see, for example, U.S. Pat. Nos. 5,116,817; 4,476,116). However, it is unknown if intranasal delivery of a composition containing multiple active agents, such as a GnRH compound and one or more hormonal agents, is suitable for contraception or for treatment of benign gynecological disorders. For example, it is unknown if the presence of multiple agents in the formulation interfere with absorption of one or another of the agents. Formulations comprised of a GnRH compound and one or more hormonal agents that are sufficiently non-irritating to the nasal mucosa for commercial viability have also not been described.

SUMMARY OF THE INVENTION

Accordingly, it is an object of the invention to provide a nasal preparation having a GnRH compound and an estrogenic compound, and optionally an androgenic compound, where uptake of the GnRH compound in the presence of the estrogenic and optional androgenic compounds is sufficient for therapeutic activity; i.e., uptake of the GnRH compound is substantially unhindered by the steroids.

It is another object of the invention to provide a bolus-form of delivery of a composition comprised of a GnRH compound and an estrogenic compound, and optionally an androgenic compound, that offers a therapeutic activity similar to that of a slow-release composition of the same active agents, with similar hormonal areas under the curve.

In one aspect, the invention includes a nasal spray formulation for use in female contraception or in the treatment of benign gynecological disorders, the composition comprising an aqueous medium having dissolved therein (i) a GnRH compound and (ii) an estrogenic compound present in the form of a water-soluble complex with a water-soluble cyclodextrin. The concentration of GnRH compound and estrogenic compound in the formulation are effective, when administered daily in the form of a liquid aerosol having a total liquid volume between 30 and 200 µL, and over an extended period of administration, to suppress ovarian estrogen and progesterone production and to prevent signs and symptoms of estrogen deficiency, without a significant increase in the risk of endometrial hyperplasia.

The GnRH compound can be an agonist or an antagonist, and exemplary compounds include deslorelin, leuprolide, nafarelin, goserelin, decapeptyl, buserelin, histrelin, gonadorelin, abarelix, cetrorelix, azaline B, and degarelix, and analogs thereof.

In one embodiment, the cyclodextrin is 2-hydroxypropyl-β-cyclodextrin and is present in the formulation at a concentration between 50 and 300 mg/mL. In another embodiment, the 2-hydroxypropyl-β-cyclodextrin has a degree of substitution between 2 and 8, more preferably between 5 and 8.

In a preferred embodiment, the GnRH compound is deslorelin, at a daily dose between 0.025 and 1.5 mg.

In another preferred embodiment, the estrogenic compound is 17-β-estradiol, at a daily dose between 0.15 and 0.6 mg.

In another embodiment, the formulation further includes testosterone as a second or third steroid in the form of a water-soluble complex with the cyclodextrin, and at a daily dose of between 0.15 and 1 mg.

In still another embodiment, the formulation further includes a progestin as a second or third steroid in the form of a water-soluble complex with the cyclodextrin.

The estrogenic compound and the second and or third steroid can have a combined molar occupancy with respect to the cyclodextrin that is greater than the molar occupancy achievable with any of the steroids alone.

In another aspect, the nasal preparation described above when intranasally administered as a daily bolus (i) is effective to achieve an average serum concentration over 24 hours of the estrogenic compound that is within 10% of the average serum concentration over 24 hours of the estrogenic compound when delivered transdermally and (ii) is as effective in preventing bone mineral density loss as transdermal administration of the estrogenic compound.

In another aspect, the invention includes an intranasal drug-delivery system for use in female contraception or in the treatment of benign gynecological disorders. The system is comprised of a nebulizer operable to deliver a selected volume between 30 and 200 μL of an aqueous formulation in the form of a liquid-droplet aerosol. Contained in the nebulizer is a liquid formulation composed of (i) a liquid carrier, (ii) a GnRH compound capable of suppressing ovarian estrogen and progesterone production, and (iii) an estrogenic compound capable of preventing signs and symptoms of estrogen deficiency when co-administered with the GnRH compound. The concentration of GnRH compound and estrogenic compound in the formulation are effective, when administered once daily in the form of a liquid aerosol having a total liquid volume between 30 and 200 μL, and over an extended period of administration, to suppress ovarian estrogen and progesterone production and to prevent signs and symptoms of estrogen deficiency, without a significant increase in the risk of endometrial hyperplasia.

These and other objects and features of the invention will be more fully appreciated when the following detailed description of the invention is read in conjunction with the accompanying examples and drawings.

DETAILED DESCRIPTION OF THE INVENTION

I. Definitions

Figure 1:
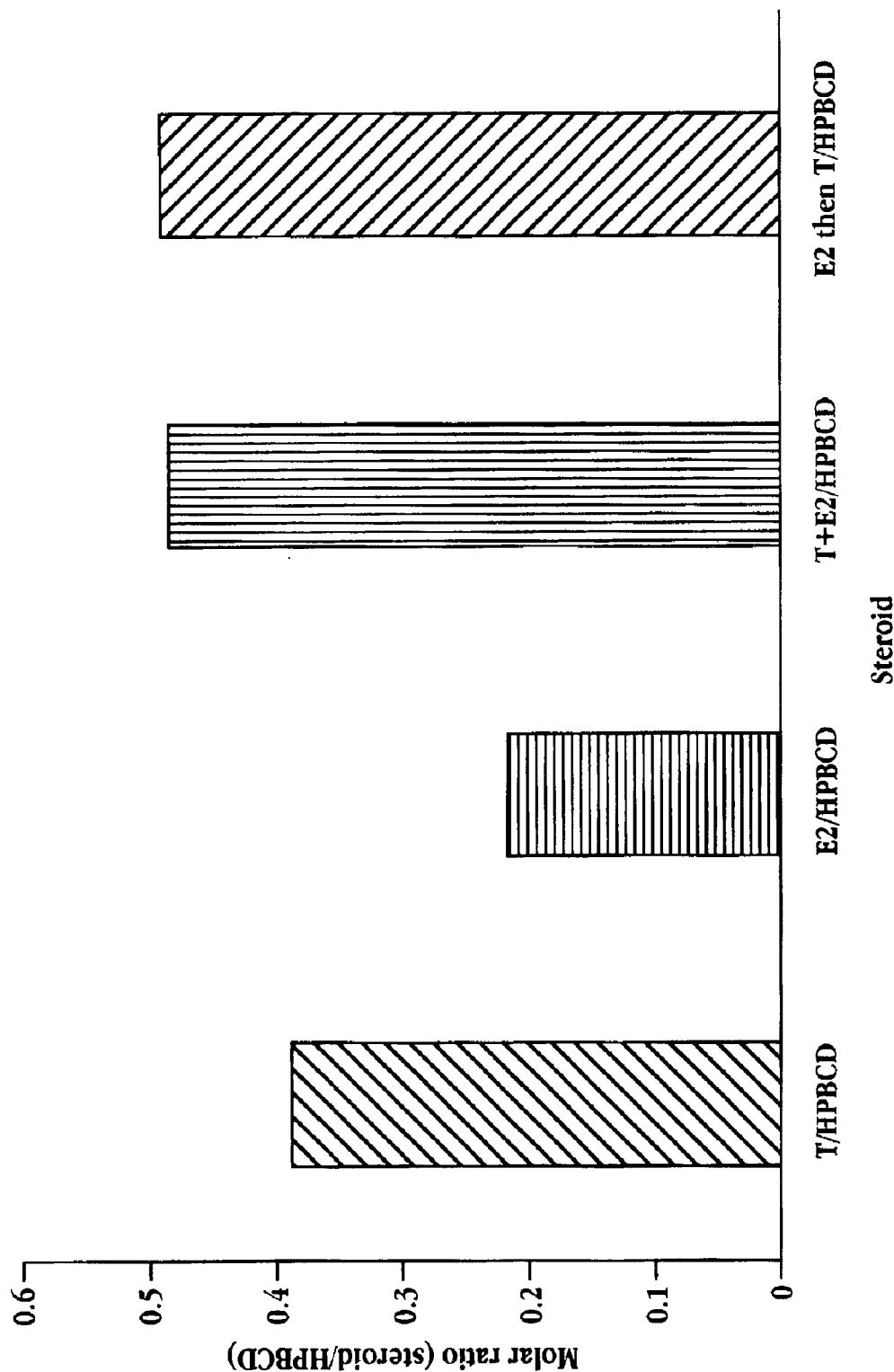
FIG. 1 is a bar graph showing the molar ratio of steroid to 2-hydroxypropyl-β-cyclodextrin for testosterone (T/HPβCD), for estradiol (E2/HPβCD), and for testosterone and estradiol in combination where the two steroids are added to the 2-hydroxypropyl-β-cyclodextrin solution simultaneously (T+E2/HPβCD) or added sequentially (E2 then T/HPβCD).

An "extended time period" intends a period of more than about 4 months, preferably more than about 6 months.

The phrase "amount effective to suppress ovarian estrogen and progesterone production" refers to a dose of a therapeutic compound, and in particular to a dose of a GnRH compound, that reduces serum estrogen levels such that one or more symptoms typically associated with menopause, such as vasomotor instability, bone loss, decreased libido, vaginal dryness, and/or urogenital atrophy, are observed. Typically, a sustained serum estrogen level of less than about 30 pg/mL, more typically of less than about 20 pg/mL, is considered as evidence that ovarian estrogen production is suppressed.

The phrase "amount effective to suppress ovarian progesterone production" refers to a dose of a therapeutic compound, and in particular to a dose of a GnRH compound, that maintains serum progesterone at a level consistent with anovulation. Typically, a sustained serum progesterone level of less than about 80 ng/dL, more typically of less than about 50 ng/dL, is considered as evidence that ovarian progesterone production is suppressed.

The phrase "amount effective to prevent signs and symptoms of estrogen deficiency" refers to a dose of a therapeutic compound that inhibits or minimizes clinically-recognized markers of estrogen deficiency, including but not limited to symptoms typically associated with menopause, such as vasomotor instability, bone loss, and/or urogenital atrophy.

The phrase "without significant risk of endometrial hyperplasia" intends a risk of developing simple endometrial hyperplasia that is less than the average risk of a given population of women. For example, the average risk of hyperplasia after one year of treatment with unopposed estrogen in the general population of postmenopausal (naturally or surgically menopausal) women treated with unopposed estrogen (0.625 mg dose) is about 30% (Gefland, M. et al. *Obstetrics & Gynecology*, 74:398 (1989)). Thus, 'no significant risk of endometrial hyperplasia', with respect to postmenopausal women treated with 0.625 mg daily unopposed estrogen, would be less than 30%, more preferably less than 20%, still more preferably less than 10%, even still more preferably less than 5%, of a test population developing simple endometrial hyperplasia.

The term "GnRH compound" as used herein intends peptide and non-peptide GnRH analogs, and includes agonists and antagonists. Exemplary non-peptide analogs are described, for example, in U.S. Pat. No. 6,346,534, and these exemplary non-peptide analogs are incorporated by reference herein. Peptide analogs are widely reported in the literature.

The terms "progestin" and "progestogen" are used interchangeably.

II. Nasal Formulation

As noted above, the invention includes a nasal preparation for use in female contraception or in the treatment of benign gynecological disorders. In this section, each component in the composition will be described.

A1. Composition Components: GnRH Compound

The composition for use in the method of the invention comprises a GnRH compound. Native GnRH is a decapeptide comprised of naturally-occurring amino acids having the L-configuration, except for the achiral amino acid glycine. The sequence of GnRH is (pyro)Glu-His-Trp-Ser-Tyr-Gly-Leu-Arg-Pro-Gly-NH$_2$ (SEQ ID NO:1). A large number of analogs of this natural peptide have been prepared and are effective to inhibit the release and/or the action of GnRH. Analogs having agonist and antagonist activity have been described, and as used herein, the term "a GnRH compound" or "GnRH compounds" intends agonists and antagonists, synthetically prepared or naturally-occurring, peptide and non-peptide compounds alike. The following description focuses in particular on GnRH agonists, however, it will be appreciated that native GnRH, GnRH antagonists, such as azaline B, abarelix, cetrorelix, and degarelix, and other GnRH analogs are also suitable for use in the composition and method of treatment. Further, the following discussion focuses on peptide analogs, however, it will be appreciated that non-peptide compounds, such as those disclosed in U.S. Pat. No. 6,346,534, are also contemplated.

GnRH agonists are compounds that work in two phases. The first phase stimulates the ovaries to produce more estradiol. During the second phase, the messenger hormones that control the ovaries are suppressed, resulting in a drop in estrogen. An exemplary agonist is obtained by changing the 6-position residue in the naturally-occurring GnRH from Gly to a D-amino acid, to give a GnRH analog having a sequence (pyro)Glu-His-Trp-Ser-Tyr-X-Leu-Arg-Pro-Gly-NH$_2$ (SEQ ID NO:2), where X represents an amino acid in the D-configuration. When X is D-Leu the analog is known as Lupron™ and is commercially available from TAP Pharmaceuticals (Lake Forest, Ill.). Agonists often have the N-terminus prolyl modified with an n-ethylamide addition. For example, the agonist deslorelin is (pyro)Pro-His-Trp-Ser-Tyr-DTrp-Leu-Arg-Pro-ethylamide (SEQ ID NO:3). Another exemplary analog is where the 6-position residue is D-Ala to give a peptide having the following sequence: (pyro)Glu-His-Trp-Ser-Tyr-D-Ala-Leu-Arg-Pro-Gly-NH$_2$ (SEQ ID NO:4; U.S. Pat. No. 4,072,668). Another exemplary agonist is obtained by eliminating the Gly-NH$_2$ in position 10 to give a nonapeptide as an alkyl, cycloalkyl, or fluoroalkylamide, or by replacing Gly-NH$_2$ by an α-azalglycine amide. Modifications to the naturally-occurring GnRH sequence at positions 1 and 2 are also possible. A number of GnRH agonists are described in the art, many of which are commercially available, and include deslorelin, leuprolide, nafarelin, goserelin, decapeptyl, buserelin, histrelin, and gonadorelin, and analogs thereof.

The dose of the GnRH compound is preferably sufficient to suppress ovarian estrogen and progesterone production, so that estrogen effects are predictably related to the co-administered estrogenic compound, described below. The amount of GnRH compound effective to achieve the desired suppression of ovarian estrogen production may readily be determined with respect to any given GnRH compound and for any given mammal. The dose range depends upon the particular GnRH compound used and may also depend upon patient characteristics, such as age and weight. Further, the effective amount of GnRH compound also depends upon route of administration. Determination of an effective dose range after consideration of these factors is routine for those of skill in the art.

By way of example of a specific formulation, the amount of GnRH compound in a daily nasal spray formulation with a volume between about 30 to about 200 µL can deliver a daily dose of GnRH compound of between about 0.025 mg to about 1.5 mg. It will be appreciated that the daily spray volume can be administered in one, two, or more separate deliveries to achieve the desired total daily spray volume. It will further be appreciated that the spray volume and the amount of GnRH compound in the nasal formulation are each individually adjustable to achieve the desired daily dosage.

A2. Composition Components: Estrogenic Compound

A second component in the composition for use in the method of the invention is an effective amount of an estrogenic compound. The estrogenic compound, is effective to prevent symptoms and signs of estrogen deficiency including bone loss, vaginal atrophy, and hot flashes.

The estrogenic compound can be a single-component natural or synthetic estrogen composition, or a combination of such compounds. As used herein, the term "estrogenic compound" refers to both natural and synthetic materials having activity to mitigate the signs and symptoms of estrogen deficiency. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, and tibolone. Equine estrogens, such as equilelinin, equilelinin sulfate, and estetrol, and synthetic steroids combining estrogenic, androgenic, and progestogenic properties such as tibolone may also be employed.

Typical dose ranges for estrogenic compounds depend on the compound and on the characteristics of the patient. For an adult human female patient treated with a transdermal 17-β-estradiol preparation, a typical dose range is one that maintains a serum level of estradiol of about 25 pg/mL to about 140 pg/mL, more preferably between about 30 pg/mL to about 50 pg/mL. A specific example of a composition containing an estrogenic compound is one comprised of a GnRH agonist and 17-β-estradiol. The two compounds, along with other optional excipients and/or a progestin and/or an androgenic compound, are formulated for delivery intranasally. For an intranasal preparation, a preferred daily dosage range for 17-β-estradiol is between about 0.15 mg and 0.6 mg.

As discussed below, the estrogenic compound is preferably co-administered from the same delivery vehicle or via the same route as the GnRH compound. However, delivery of the estrogenic compound can be from a different vehicle and/or by a different route than the GnRH compound, and some examples of such "mixed modes" of administration are provided below.

A3. Composition Components: Androgenic Compound

The composition comprised of a GnRH compound and an estrogenic compound can optionally include an androgenic compound. When present in the composition, the androgenic compound is in an amount effective to increase a patient's androgen level to a level not exceeding a "normal" premenopausal level, and in particular in concert with the estrogenic composition to maintain bone mineral density. Such "normal" androgen levels are on the order of about 15 ng/dL to about 80 ng/dL for testosterone.

Suitable androgenic compounds for use in the composition include but are not limited to testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, and stanozolol.

Typical dose ranges for androgenic hormones depend upon the choice of compound and the individual patient. For an adult human female administered testosterone, typical doses are administered to provide serum levels of testosterone of from about 15 ng/dL to about 80 ng/dL, and preferably about 40 ng/dL to about 60 ng/dL. A typical daily dose can range from between about 0.15 mg to about 1 mg. A specific example of a composition containing an androgenic compound is one comprised of a GnRH agonist and 17-β-estradiol and testosterone. The compounds, along with other optional excipients, are formulated for delivery intranasally, and exemplary formulations are described below.

A4. Composition Components: Progestin Compound

The composition comprised of a GnRH compound and an estrogenic compound, in some embodiments, can further include a progestin. Formulations that include a progestin can be administered for a limited period of time, for example on the order of 5 to 20 days, and preferably 10 to 15 days after each extended treatment regimen of, for example, about 4 months, more preferably greater than about 6 months, and more specifically, of from about 4 months to about 12 months. The progestin is provided in an amount effective to minimize or eliminate the occurrence of endometrial hyperplasia by substantially reducing the possibility of endometrial hyperstimulation which may occur during prolonged treatment with estrogenic steroids without a progestin.

Suitable progestational agents (progestins) include but are not limited to dydrogesterone, ethynodiol diacetate, hydroxyprogesterone caproate, medroxyprogesterone acetate, norethindrone, norethindrone acetate, norethynodrel, norgestrel, progesterone, and megestrol acetate. Typical dose ranges for progestins depend upon the choice of steroid and the individual patient. Doses are selected as adequate to produce a secretory uterine endothelium after the time interval of progestogen treatment (about 5 to about 20 contiguous days, and preferably about 10 to about 15 contiguous days). The serum level of progesterone is generally less than about 50 ng/dL after the time interval of progestin treatment.

B. Exemplary Nasal Preparations

As noted above, the composition comprised of a GnRH compound, and estrogenic compound, and optionally an androgen and/or a progestin, is mucosally administered by contacting the composition in a suitable dosage form with mucosal tissue of the vagina, nose, rectum, or mouth. In a preferred embodiment, the composition is administered via the nasal mucosa, i.e., intranasally. The nasal mucosa provides a useful anatomical site for systemic delivery. The nasal tissue is highly vascularized, providing an attractive site for rapid and efficient absorption. The adult nasal cavity has a capacity of around 20 mL, with a large surface area of approximately 180 cm$^2$ for drug absorption, due in part to the microvilli present along the psuedostratified columnar epithelial cells of the nasal mucosa.

A nasal preparation comprised of the composition described above can take a variety of forms for administration in nasal drops, nasal spray, gel, ointment, cream, powder or suspension, using a dispenser or other device as needed. A variety of dispensers and delivery vehicles are known in the art, including single-dose ampoules, atomizers, nebulizers, pumps, nasal pads, nasal sponges, nasal capsules, and the like.

More generally, the preparation can take a solid, semi-solid, or liquid form. In the case of a solid form, the components may be mixed together by blending, tumble mixing, freeze-drying, solvent evaporation, co-grinding, spray-drying, and other techniques known in the art. Such solid state preparations preferably provide a dry, powdery composition with particles in the range of between about 20 to about 500 microns, more preferably from 50 to 250 microns, for administration intranasally.

A semi-solid preparation suitable for intranasal administration can take the form of an aqueous or oil-based gel or ointment. For example, the components described above can be mixed with microspheres of starch, gelatin, collagen, dextran, polylactide, polyglycolide or other similar materials that are capable of forming hydrophilic gels. The microspheres can be loaded with drug, and upon administration form a gel that adheres to the nasal mucosa.

In a preferred embodiment, the nasal preparation is in liquid form, which can include an aqueous solution, an aqueous suspension, an oil solution, an oil suspension, or an emulsion, depending on the physicochemical properties of the composition components. The liquid preparation is administered as a nasal spray or as nasal drops, using devices known in the art, including nebulizers capable of delivering selected volumes of formulations as liquid-droplet aerosols. For example, a commercially available spray pump with a delivery volume of 50 or 100 μL is available from, for example, Valois (Congers, N.Y.) with spray tips in adult size and pediatric size. In one embodiment, the composition comprised of a GnRH agonist and an estrogenic compound are co-administered intranasally via an aerosol spray in a daily volume of between about 30 to about 200 μL.

The liquid preparation can be produced by known procedures. For example, an aqueous preparation for nasal administration can be produced by dissolving, suspending, or emulsifying the polypeptide and the steroid compounds in water, buffer, or other aqueous medium, or in a oleaginous base, such as a pharmaceutically-acceptable oil like olive oil, lanoline, silicone oil, glycerine, fatty acids, and the like.

It will be appreciated that excipients necessary for formulation, stability, and/or bioavailability can be included in the preparation. Exemplary excipients include sugars (glucose, sorbitol, mannitol, sucrose), uptake enhancers (chitosan), thickening agents and stability enhancers (celluloses, polyvinyl pyrrolidone, starch, etc.), buffers, preservatives, and/or acids and bases to adjust the pH.

In a preferred embodiment, an absorption promoting component is included. Exemplary absorption promoting components include surfactant acids, such as cholic acid, glycocholic acid, taurocholic acid, and other cholic acid derivatives, chitosan and cyclodextrins. In a preferred embodiment, a cyclodextrin is included in the preparation. Cyclodextrins are cyclic oligosaccharides of α-D-glucopyranose and can be formed by the catalytic cyclization of starch. Due to a lack of free rotation about the bonds connecting the glycopyranose units, cyclodextrins are toroidal or cone shaped, rather than cylindrical. The cyclodextrins have a relatively hydrophobic central cavity and a hydrophilic outer surface. The hydrophobic cage-like structure of cyclodextrins has the ability to entrap a variety of guest compounds to form host-guest complexes in the solid state and in solution. These complexes are often termed inclusion complexes and the guest compounds are released from the inclusion site.

The most common cyclodextrins are α-, β-, and γ-cyclodextrin, which consist of six, seven, or eight glucopyranose units, respectively. Cyclodextrins containing nine, ten, eleven, twelve, and thirteen glucopyranose units are designated δ-, ε-, ξ-, η-, and θ-cyclodextrin, respectively. Characteristics of α-, β-, γ-, and δ-cyclodextrin are shown in Table 1.

TABLE 1

Cyclodextrin Characteristics

|  | α-cyclo-dextrin | β-cyclo-dextrin | γ-cyclo-dextrin | δ-cyclo-dextrin |
|---|---|---|---|---|
| no. of glucopyranose units | 6 | 7 | 8 | 9 |
| molecular weight (Daltons) | 972 | 1135 | 1297 | 1459 |
| central cavity diameter (Å) | 4.7–5.3 | 6.0–6.5 | 7.5–8.3 | 10.3–11.2 |
| water solubility (at 25° C., g/100 mL) | 14.5 | 1.85 | 23.2 | 8.19 |

Derivatives formed by reaction with the hydroxyl groups lining the upper and lower ridges of the toroid are readily prepared and offer a means of modifying the physicochemical properties of the parent cyclodextrins. The parent cyclodextrins, and in particular β-cyclodextrin, have limited aqueous solubility. Substitution of the hydroxyl groups, even with hydrophobic moieties such as methoxy and ethoxy moieties, typically increases solubility. Since each cyclodextrin hydroxyl group differs in chemical reactivity, reaction with a modifying moiety usually produces an amorphous mixture of positional and optical isomers. The aggregate substitution that occurs is described by a term called the degree of substitution. For example, a 2-hydroxypropyl-β-cyclodextrin with a degree of substitution of five would be composed of a distribution of isomers of 2-hydroxypropyl-β-cyclodextrin in which the average number of hydroxypropyl groups per 2-hydroxypropyl-β-cyclodextrin molecule is five. Degree of substitution can be determined by mass spectrometry or nuclear magnetic resonance spectroscopy. These methods do not give information as to the exact location of the substituents (C1, C2, C3, etc.) or the distribution of the substituents on the cyclodextrin molecule (mono, di, tri, poly). Theoretically, the maximum degree of substitution is 18 for α-cyclodextrin, 21 for β-cyclodextrin, and 24 for γ-cyclodextrin, however, substituents with hydroxyl groups present the possibility for additional hydroxylalkylations.

The cyclodextrin used in the present invention is preferably an α-, β-, or γ-cyclodextrin. The cyclodextrin selected for use depending on which cyclodextrin binds the guest compounds and yields the desired bioavailability. In a preferred embodiment, a derivative of a cyclodextrin is selected, and derivatives such as hydroxypropyl, dimethyl, and trimethyl substituted cyclodextrins are contemplated, as are cyclodextrins linked with sugar molecules, sulfonated cyclodextrins, carboxylated cyclodextrins, and amino derivatives such as diethylamino cyclodextrins. In a preferred embodiment, the cyclodextrin is a β-cyclodextrin, and in a more preferred embodiment, the cyclodextrin is 2-hydroxypropyl-β-cyclodextrin. In yet another embodiment, the 2-hydroxypropyl-β-cyclodextrin has a degree of substitution between 2 and 8, more preferably between 4 and 8, most preferably between 5 and 8.

In a study performed in support of the invention, the solubility of the steroids estradiol and testosterone, alone and in combination, in varying concentrations of 2-hydroxypropyl-β-cyclodextrin was determined. As described in Example 1, defined amounts of each steroid were added to 1 mL of 2-hydroxypropyl-β-cyclodextrin in water. The solubility of the steroids was determined, and the results are shown in Tables 2A and 2B.

Table 2A shows the solubility of 17-β-estradiol and testosterone individually in aqueous solutions of 2-hydroxypropyl-β-cyclodextrin. The last two columns in the Table 2A show the molar ratio of each steroid to the cyclodextrin. The molar occupancy of 17-β-estradiol with respect to 2-hydroxypropyl-β-cyclodextrin, averages approximately 0.21. The molar occupancy of testosterone with respect to 2-hydroxypropyl-β-cyclodextrin averages approximately 0.39.

TABLE 2A

Solubility of 17-β-Estradiol and Testosterone in 2-Hydroxypropyl-β-cyclodextrin

|  | 17-β-Estradiol | Testosterone | Molar Ratio | |
|---|---|---|---|---|
| HPβCD* mg/mL | solubility mg/mL | solubility mg/mL | Estradiol/ HPβCD | Testosterone/ HPβCD |
| 10 | 0.414 | 0.810 | 0.21 | 0.39 |
| 40 | 1.605 | 2.541 | 0.20 | 0.30 |
| 70 | 2.763 | 5.626 | 0.20 | 0.38 |
| 100 | 4.062 | 6.819 | 0.21 | 0.33 |
| 130 | 5.494 | 11.649 | 0.21 | 0.43 |
| 160 | 6.841 | 13.866 | 0.22 | 0.41 |
| 190 | 8.379 | 16.522 | 0.22 | 0.42 |
| 220 | 9.330 | 18.604 | 0.21 | 0.40 |
| 250 | 11.031 | 21.684 | 0.22 | 0.41 |

*2-hydroxypropyl-β-cyclodextrin

Table 2B shows the solubility of 17-β-estradiol as a first steroid and testosterone as a second steroid in aqueous 2-hydroxypropyl-β-cyclodextrin. The last three columns show the molar ratios of each steroid individually in the 2-hydroxypropyl-β-cyclodextrin solution and of the two steroids together in the solution. The data shows that the combined molar occupancy of the two steroids together, average approximately 0.48, is greater than the molar occupancy achieved with either steroid alone (Table 2A).

TABLE 2B

Molar Occupancy of 17-β-Estradiol and Testosterone in 2-Hydroxypropyl-β-cyclodextrin

|  | Estradiol and Testosterone solubility mg/mL | | Molar Ratio | | |
|---|---|---|---|---|---|
| HPβCD* mg/mL | Estradiol | Testosterone | Estradiol/ HPβCD | Testos- terone/ HPβCD | Estradiol & Testosterone/ HPβCD |
| 10 | 0.164 | 0.658 | 0.08 | 0.31 | 0.40 |
| 40 | 0.834 | 2.819 | 0.11 | 0.34 | 0.44 |
| 70 | 1.562 | 5.073 | 0.11 | 0.35 | 0.46 |
| 100 | 2.157 | 7.113 | 0.11 | 0.34 | 0.45 |
| 130 | 3.202 | 10.552 | 0.12 | 0.39 | 0.51 |
| 160 | 4.053 | 13.422 | 0.13 | 0.40 | 0.53 |
| 190 | 4.796 | 15.742 | 0.13 | 0.40 | 0.52 |
| 250 | 5.774 | 19.986 | 0.12 | 0.38 | 0.50 |

*2-hydroxy-propyl-β-cyclodextrin

The molar ratio data of Tables 2A and 2B are presented graphically in FIG. 1. The figure also shows the molar ratio determined in another study where estradiol was first added to the aqueous 2-hydroxypropyl-β-cyclodextrin solution, followed by addition of testosterone. The molar occupancy of the two steroids in combination is similar, regardless of the sequence of addition of the steroids to the 2-hydroxypropyl-β-cyclodextrin solution.

In another study, the solubility of 17-β-estradiol and testosterone, alone and in combination, as a function of degree of substitution of 2-hydroxypropyl-β-cyclodextrin was evaluated. Solutions of 2-hydroxypropyl-β-cyclodextrin with degrees of substitution of 5.5, 6.1, and 6.8 were prepared and the maximum concentration of estradiol and testosterone that could be solubilized was determined. There was a slight trend for the 2-hydroxypropyl-β-cyclodextrin with a lower degree of substitution to solubilize more steroid, however, the trend was not statistically significant.

C. In vivo Studies

In studies performed in support of the invention, the GnRH compound deslorelin and the estrogenic compound estradiol, in the form of a water-soluble complex with the cyclodextrin 2-hydroxypropyl-β-cyclodextrin, were administered intranasally to patients. These studies will now be described.

In a first study, deslorelin was administered alone to determine an appropriate dose for treatment of an exemplary benign gynecological disorder, uterine leiomyomata (fibroids). More specifically, the dose appropriate to control the heavy bleeding secondary to uterine leiomyomata was determined. As described in Example 3, female patients were treated with deslorelin administered daily via intranasal delivery, at a dose of 0.5 mg, 1.0 mg or 2.0 mg. The compound was administered using a commercially available nasal sprayer that delivered a 50 μL spray volume. The daily dose was administered by application of 50 μL to each nostril once per day, for a total daily volume of 100 μL. During the 12 week treatment period the patients kept daily bleeding calendars and underwent clinical assessments at scheduled intervals. Clinical assessments included grading of nasal irritation (Table 5A), determination of uterine size (Table 5B), and serum hormone levels (Table 5C). This clinical data are presented in the indicated tables in Example 3, along with the bleeding scores (Table 5D).

With respect to nasal irritation, the data (Table 5A in Example 3) indicates that subjects experience none or slight irritation at doses of 0.5 mg and 1 mg. Some of the subjects treated with a deslorelin dose of 2 mg experienced more frequent irritation.

Table 5B in Example 3 also shows a reduction in uterine volume (calculated from ultrasound determined dimensions), with the reduction directly correlating to dose.

Serum levels of estradiol, progesterone, and testosterone are shown in Table 5C in Example 3. Reduction in estradiol levels was progressive and dose dependent over the 12 week period. Progesterone levels followed a similar pattern with progressive suppression with higher dose and longer time. Testosterone levels were also similar.

With respect to bleeding scores (Table 5D in Example 3), the patients treated with the GnRH compound had a marked improvement in their bleeding score at the end of the 12 week study.

In summary, all tested doses were partially or completely effective with reduction of bleeding, associated pain, and uterine size. This effect correlates with a reduction of estrogen and progesterone. Based on the bleeding scores, a 1 mg dose appears to offer a slight advantage compared with the 0.5 mg dose. Uterine size and rates of change of estrogen and testosterone levels are clearly dose related over the range studied.

Another study performed in support of the invention is described in Example 4. In this study, the GnRH compound deslorelin, estradiol, and testosterone were co-administered as an "all-in-one" nasal spray to oophorectomized women. Each woman was treated with 50 μL of a nasal spray preparation, prepared as described in Example 2, delivered as a single dose on two occasions separated by one week. The 50 μL dose delivered 1 mg deslorelin, 50 μg estradiol, and 250 μg testosterone. The estradiol and testosterone were in the form of a water-soluble complex with cyclodextrin. Blood samples were collected prior to and after dosing on each test day for quantitation of serum estradiol and testosterone levels. The results are presented in FIGS. 2A and 2B.

Figure 2A:
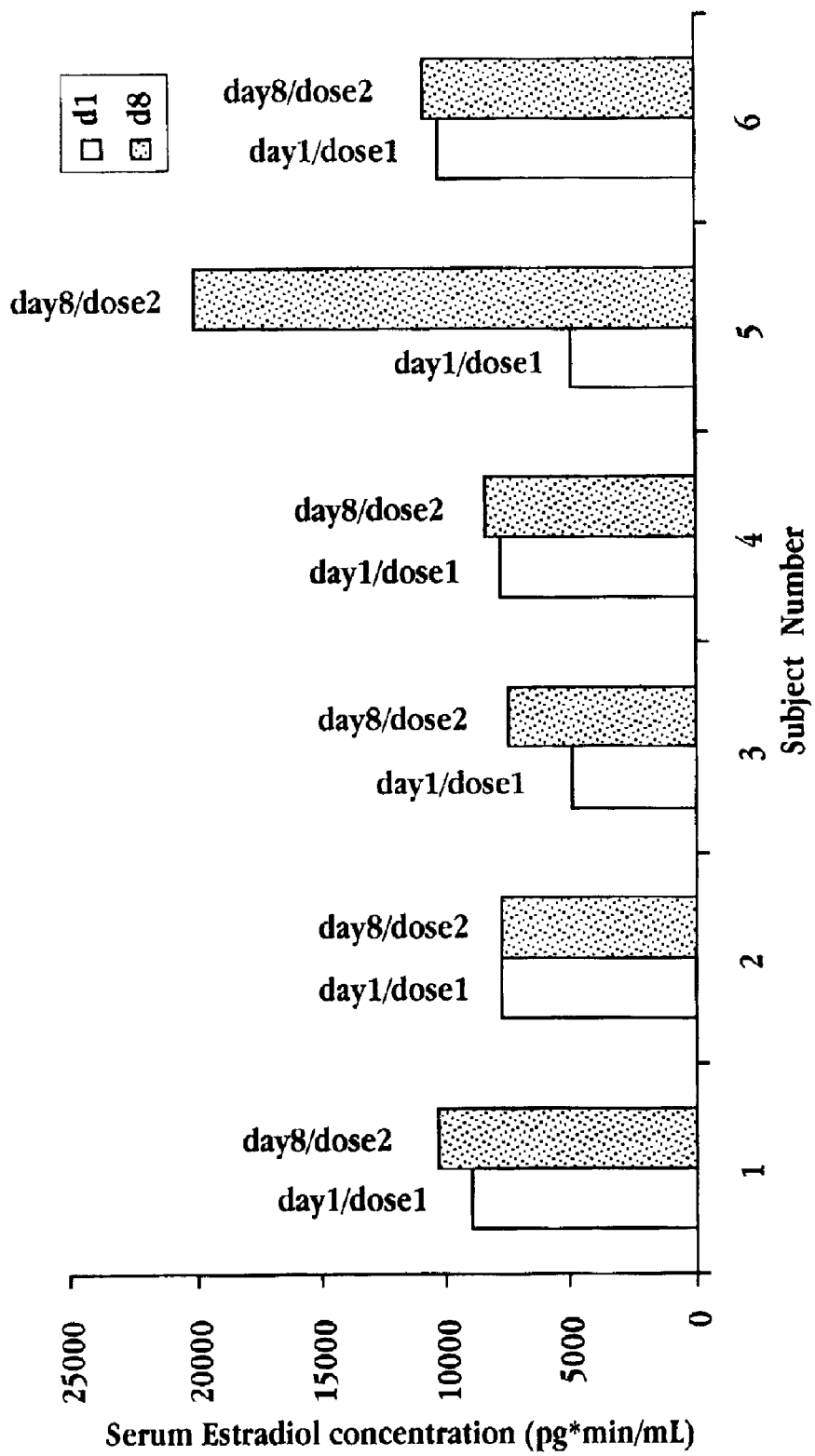
FIGS. 2A–2B are bar graphs showing the baseline corrected cumulative area under the curve from 0 to 360 minutes of serum estradiol in pg·min/mL (FIG. 2A) and of serum testosterone in ng·min/dL (FIG. 2B) for six patients treated with an intranasal preparation comprised of the GnRH compound deslorelin, estradiol, and testosterone. The preparation was administered twice (days 1 and 8), one week apart.
Figure 2B:
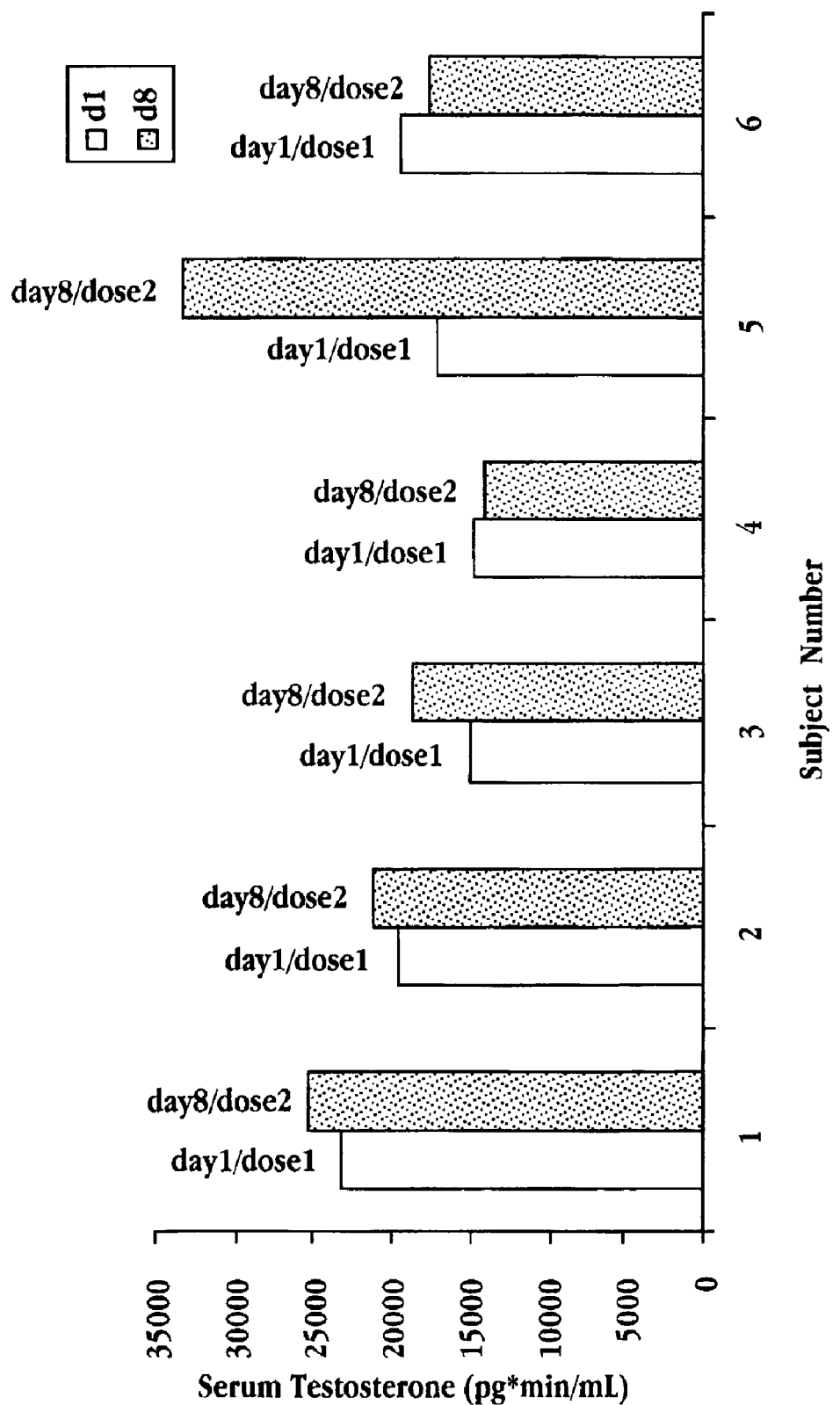

FIG. 2A is a bar graph showing the cumulative area under the curve (AUC) from 0 to 360 minutes for serum estradiol, in pg*min/mL, for each of the six patients. FIG. 2B is a similar graph for testosterone. The hormone levels on day 1 and day 8, corresponding to dose 1 and dose 2, are shown as a separate bar for each patient. Comparison of the AUC of each patient shows that uptake of the compounds in the nasal preparation is relatively uniform, with variations between patients likely due to varying extent of metabolic conversion during nasal mucosa absorption. Importantly, the data also show that significant absorption of estradiol and testosterone occurs in the presence of the GnRH compound.

Example 5 describes a study performed in support of the invention where the nasal preparation similar to that of Example 2, comprised of a GnRH compound, estradiol, and testosterone, was administered to normal premenopausal women. Three doses of the GnRH compound deslorelin were tested, 0.5 mg, 1.0 mg, and 2.0 mg. The nasal preparation was administered using a conventional metered nasal spray delivery device. The subjects received two 50 μL sprays, one in each nostril, daily for four weeks. Blood samples were collected prior to drug administration on day 1 of the study, and then at regular intervals throughout day 1. Thereafter, blood samples were collected weekly, until day 29, when blood was collected at scheduled intervals throughout the day. Serum deslorelin, estradiol, testosterone, and progesterone were quantified, and the results are shown in Tables 6A through 6C.

The degree of induced ovarian suppression is evident from the serum estradiol and progesterone levels (Tables 6A–6C). Serum levels of estradiol on day 29 varied from 14 pg/mL to 103 pg/mL. Progesterone levels were generally less than 80 ng/dL during the treatment interval indicating that women were anovulatory during the treatment.

In one embodiment, the intranasal dose of the estrogenic compound, and the optional androgen if present, achieve a transient serum level outside the serum estradiol level of between about 25 pg/mL to about 140 pg/mL that is typically reported in the literature with a 50 μg/day transdermal patch. Although the hormonal serum levels resulting from intranasal delivery of the hormone(s) are transiently outside this range a similar beneficial effect is achieved. That is, the biological effect(s) resulting from intranasal delivery of an estrogenic compound, and the optional androgen, is similar to the biological effect associated with a serum estradiol level of between about 25 pg/mL to about 140 pg/mL even though the actual transient serum level may be outside this range. Thus, in one embodiment, the invention contemplates administration of an estrogenic compound and an optional androgen in an amount sufficient to achieve the beneficial biological effects that are associated with a steady serum estradiol level of between about 25 pg/mL to about 140 pg/mL, more preferably between about 30 pg/mL to about 100 pg/mL, most preferably, between about 30 pg/mL to about 50 pg/mL. In intranasal formulations where the optional androgen is present, the transient androgen serum blood level achieved may be lower or higher than that typically obtained by other routes of administration. However, the beneficial effects achieved by intranasal administration are similar to those obtained from a steady serum testosterone level of between about 20 ng/dL to about 80 ng/dL, more preferably between about 40 ng/dL to about 60 ng/dL.

A comparison of the total area under concentration-time curves (AUC) or average concentrations of serum estradiol (or testosterone) in subjects treated with intranasal estradiol (or testosterone) and patients treated with estradiol (or testosterone) by another route, such as oral, provides a basis for determining the biological equivalency of different routes of administration. Where the AUCs or average concentrations are similar, despite different routes of administration or different concentration-time profiles, the biological effect achieved is often similar. Thus, in one embodiment, the invention contemplates achieving by intranasal administration of the disclosed composition an average serum estradiol concentration over 24 hours of between about 25 pg/mL and about 50 pg/mL. In nasal preparations containing the optional androgen testosterone, the invention contemplates achieving an average serum testosterone concentration over 24 hours of between about 15 ng/dL and about 40 ng/dL.

In a study performed in support of the invention, the average concentration over 24 hours resulting from transdermal administration of estradiol and from intranasal administration of estradiol were compared. As described in Example 6, test subjects received estradiol transdermally or intranasally. Transdermal estradiol was administered using a Noven Vivelle® or a Noven Vivelle-dot® transdermal patch, both at dosages of 50 pg/day. The subjects treated intranasally received 350 μg estradiol in a liquid spray delivered once per day. Average concentrations for each of the patient populations were determined from blood samples, and the results are summarized in Table 7 below in Example 6.

The average serum estradiol concentration over 24 hours for women receiving estradiol transdermally from the Vivelle® patch was 34.4 pg/mL and from the Vivelle-dot® patch was 36.8 pg/mL. The average estradiol concentration for women treated with intranasal estradiol was 37.8 pg/mL. This study shows that an estrogenic compound administered as an intranasal bolus achieves a 24 hour average serum concentration comparable to that achieved by transdermal administration. Thus, in one embodiment the invention provides a 24 hour average serum concentration of estradiol from an intranasal bolus dose of estradiol that is within (plus or minus) about 10% of the 24 hour average estradiol serum concentration achieved from transdermal estradiol administration. That is, the 24 hour average estradiol serum concentration from intranasal bolus administration of estradiol is at least about 90% of the 24 hour average estradiol serum concentration from transdermal administration of estradiol. This result was surprising since heretofore it was unknown (i) if a bolus dose would achieve efficacious blood concentration and (ii) if a bolus dose would achieve a concentration comparable to that of a controlled-release transdermal dose. The data shows that an intranasal bolus dose of an estrogenic compound achieves a therapeutic blood concentration, and that the concentration is comparable,i.e., is within at least about 10%, to that achieved by transdermal administration of the estrogenic compound.

In another study, five women were treated with intranasal testosterone. In this study, 250 μg testosterone was formulated into a nasal preparation also containing deslorelin and estradiol (Example 2). The formulation was administered initially on day 1 of the study, and then again one week later on day 8 of the study. The average serum concentrations over 24 hours are shown in Table 3.

TABLE 3

Testosterone: Average Concentration over 24 Hours after Intranasal Administration of 250 μg

| Subject Number | Treatment Day | Testosterone (average concentration over 24 hours, ng/dL) |
|---|---|---|
| 1 | Day 1 | 26.7 |
|   | Day 8 | 24.1 |
| 2 | Day 1 | 26.7 |
|   | Day 8 | 29.9 |
| 3 | Day 1 | 19.0 |
|   | Day 8 | 17.1 |
| 4 | Day 1 | 18.8 |
|   | Day 8 | 16.5 |
| 5 | Day 1 | 19.1 |
|   | Day 8 | 16.2 |
| Average of both observations in each of the 5 subjects | | 21.4 |

The average concentration over 24 hours for both doses in the five subjects was 21.4 ng/dL. This concentration is comparable to literature reported values achieved from transdermal administration of testosterone. For example, in Javanbakhtet al. (*J. of Clinical Endocrinology and Metabolism*, 85(7): 2935, 2000) women wearing a transdermal testosterone patch for 96 hours that delivered 300 μg/day had an average serum concentration of 15.8 ng/dL. Thus, the nasal formulation of the present invention, i.e., a bolus dose of testosterone, provides a similar area under the curve as a slow-release transdermal formulation, as evidenced by similar average concentration values.

Example 7 describes a study performed in support of the invention where the efficacy and biologic equivalence between nasal spray add-back estradiol and transdermal estradiol add-back were evaluated. Women with endometriosis treated with intranasal deslorelin (GnRH compound) were assigned to one of three methods of estradiol add-back: (1) 50 μg/day estradiol transdermal patch, (2) 300 μg/day intranasal estradiol, or (3) 300 μg/day intranasal estradiol with 275 μg/day intranasal testosterone. Treatment efficacy was measured by evaluating the decrease in endometriosis using a standard scoring system that takes into account 3 symptoms (pelvic pain, dysmenorrhea, and dyspareunia) and two signs (pelvic tenderness and pelvic induration) of endometrosis. The results are shown in Table 8A in Example 7 as the composite score physical symptoms and signs score (CPSSS) taken as the sum of the scores for each individual symptom or sign (0 to 3 with 0 being not present and 3 being the most severe). The nasal spray preparations with at least 90% of the estradiol average serum concentration (AUC) of the transdermal patch (Table 7) were more effective than the transdermal patch.

Loss of bone mineral density (BMD) is a known side effect of treatment with GnRH compounds. Thus, BMD of the lumbar spine of the test subjects in Example 7 was obtained by dual-energy X-ray absorptiometry (DEXA) prior to and after six months of treatment. The results are shown in Table 8B in Example 7 as the ratio of BMD at the six month time point ($BMD_{6mo}$) to the BMD prior to treatment ($BMD_{baseline}$). BMD of subjects treated with deslorelin alone in another study (Example 8) is also shown in Table 8B for comparison. A reduction in loss of BMD by addition of estradiol to deslorelin is apparent, since all subjects treated with estradiol had reduced bone loss. The data also shows that estradiol add-back in the form of an intranasal bolus is at least as effective, and in fact slightly more effective, in preventing loss of BMD than a transdermal estradiol add-back, as observed by comparing the BMD ratios for women receiving estradiol transdermally ($BMD_{6mo}/BMD_{baseline}$=0.978) and for women receiving estradiol intranasally ($BMD_{6mo}/BMD_{baseline}$=0.996).

The data in Tables 8A–8B demonstrate that the estradiol added-back in the form of an intranasal bolus dose to deslorelin resulted in a significant decrease in endometriosis symptoms and at the same time reduced the loss of BMD. A nasal spray preparation comprised of a GnRH compound and an estrogenic compound, where the preparation has an 24 hour average estrogenic compound serum concentration (AUC) within 10% of the 24 hour average transdermal estrogenic compound serum concentration (Table 7), was at least as effective, and preferably more effective, in preventing loss of BMD than an add-back estrogenic compound in the form of a transdermal patch.

The incidence of endometrial hyperplasia resulting from co-administration of a GnRH compound and unopposed estradiol was evaluated in a study described in Example 8. One-hundred twelve premenopausal women participated in a year long study where deslorelin was administered daily as a nasal spray and estradiol was administered in the form of a transdermal patch. At the end of the year endometrial biopsies were evaluated for hyperplasia. The results, which are shown in Table 9C (see Example 8 below), show that the incidence of simple hyperplasia for untreated subjects (Arm 1, placebo/placebo) was 2.2%. The incidence of simple hyperplasia for subjects treated with intranasal deslorelin and transdermal estradiol (Arms 3, 4 and 5) was 0% (Arms 3 and 5) or 4.2% (Arm 4). The incidence in combined Arms 4 and 5 was 2.0%. These data show that delivery of a GnRH compound with unopposed estrogen (that is, estrogen in the absence of a progestogen) resulted in little risk of endometrial hyperplasia, with the risk no greater than that of the women in the untreated population. The patients in Arm 2 of the study, where estradiol was absent for the first six months of the study and then added for the final six months, had a 16.7% incidence of hyperplasia.

In a similar study, described in Example 9, twenty women were treated with deslorelin and unopposed estradiol. The women were divided into treatment groups to receive intranasal deslorelin and intranasal estradiol (Arm 1), intranasal deslorelin and transdermal estradiol (Arm 2), or intranasal deslorelin and intranasal estradiol plus testosterone (Arm 3). At the end of the 6 month treatment period, the endometrial response was evaluated by biopsy.

The results of the biopsy are shown in Table 10 presented below in Example 9. The endometrial tissue was proliferative in the 16 evaluable biopsies, and there was no evidence of endometrial hyperplasia in any of these evaluable subjects after six months of treatment.

The studies described in Examples 8 and 9 show that women administered a GnRH compound and an estrogen, and optionally an androgen, by non-gastrointestinal routes, and preferably intranasally, are not at increased risk of endometrialhyperplasia. The data show that a GnRH compound and an estrogenic compound can be administered to premenopausal women with no increased risk of developing simple endometrial hyperplasia. This observation is unexpected since typically 30% of postmenopausal women treated with unopposed estrogen (0.625 mg dose) develop simple hyperplasia (Gefland, M. et al. *Obstetrics & Gynecology*, 74:398 (1989); *JAMA*, 275(5):370 (1996); Clisham, P. et al., *Obstetrics & Gynecology*, 79:196 (1992)). Premenopausal women treated with a GnRH compound and an estrogen were expected to be similar to postmenopausal women, since the GnRH compound reduces serum estradiol and serum progesterone levels. However, the data clearly demonstrated that premenopausal women treated with a GnRH compound and an estrogenic compound for an extended time period (e.g., up to one year) had no increased incidence of simple hyperplasia. Thus, addition of a progestin to the treatment regimen of a GnRH compound and an estrogenic compound in premenopausal women was not and is not needed to protect against simple endometrial hyperplasia. This observation is particularly seen in women who have no prior estrogen deprivation (compare Arms 3, 4, 5 with Arm 2 in the study describe in Example 5). The studies further suggest that such treatment can continue for a period of about 6 to 12 months or longer with no significant risk of developing simple hyperplasia.

Based on these studies, the phrase "no significant risk" as used herein intends that fewer than about 10%, and more preferably less than 5%, still more preferably less than about 2% of premenopausal women treated with a GnRH compound and an estrogenic compound are at risk of developing simpleendometrial hyperplasia. In summary, the studies show that treatment of benign gynecological disorders with a GnRH compound and an estrogenic compound and, optionally, an androgenic compound, or contraception with the two or three compounds, need not be accompanied by treatment with a progestin on a regular or periodic basis in order to protect against simple endometrial hyperplasia or cancer.

From the foregoing, it can be seen how various objects and features of the invention are met. Contraception and/or treatment of benign gynecological disorders by intranasal delivery of a GnRH compound and an estrogenic compound effectively suppresses ovarian estrogen and progesterone production. The nasal preparations described herein contain the estrogenic compound in the form of a water-soluble complex with a water-soluble cyclodextrin. In some embodiments, a second steroid, such as testosterone or a progestin, is included. Absorption of the GnRH compound in the presence of the steroids is adequate to achieve suppression of ovarian estrogen and progesterone production. Further, the nasal formulations tested were non-irritating to the test subjects.

The studies described herein also showed that the nasal preparation, when administered to premenopausal women not receiving exogenously supplied progesterone, did not increase the risk of simple endometrial hyperplasia, relative to women receiving placebo. The studies suggest that such treatment can continue for a period of 6 to 12 months or longer with no significant risk of simple endometrial hyperplasia.

III. Examples

The following examples further illustrate the invention described herein and are in no way intended to limit the scope of the invention.

Example 1

Solubility of Estradiol and Testosterone in Cyclodextrin/Water

The solubility of 17-β-estradiol and testosterone in varying concentrations of 2-hydroxypropyl-β-cyclodextrin (MW 1380 g/mole; 5.5 degree of substitution) was determined as follows. 10 ng 17-β-estradiol (MW 272.39 g/mole) was added to 1 mL of 2-hydroxypropyl-β-cyclodextrin in water, the 2-hydroxypropyl-β-cyclodextrin concentration ranging from 10 to 250 ng/mL. In a second series of vials, 20 ng of testosterone (MW 288.43 g/mole) was added to 1 mL of 2-hydroxypropyl-β-cyclodextrin in water, the 2-hydroxypropyl-β-cyclodextrin concentration ranging from 10 to 250 ng/mL. In a third set of vials 10 ng 17-β-estradiol and 20 ng testosterone were added to 1 mL of 2-hydroxypropyl-β-cyclodextrin in water, the 2-hydroxypropyl-β-cyclodextrin concentration ranging from 10 to 250 ng/mL. The vials were mixed at room temperature for about 1 hour. Aliquots were taken from the supernatant of each vial and assayed for steroid concentration. The results are shown in Tables 2A and 2B.

Example 2

Preparation of Intranasal Formulation

2-Hydroxypropyl-β-cyclodextrin was added to water at a concentration of 240 mg/mL and stirred until dissolved. 17-β-Estradiol was then added to the water-cyclodextrin solution at a concentration of 1.0 mg/mL. The mixture was stirred until dissolution. Testosterone at a concentration of 5.0 mg/mL was then added, and after stirring to dissolution benzalkonium chloride (0.1 mg/mL), ethylene diamine tetra acetic acid (EDTA; 1 mg/mL), and sorbitol (61.6 mg/mL) were added. The mixture was stirred. Then, the GnRH compound deslorelin acetate was added at a concentration of 20 mg/mL with stirring. The volume was brought to the final desired volume and the pH was adjusted as needed. Table 4 summarizes the preparation components, concentrations, and dosages per 50 μL.

TABLE 4

Components in Exemplary Nasal Preparation

| Component | Concentration (mg/mL) | Dose per 50 μL |
|---|---|---|
| deslorelin acetate | 20 | 1.0 mg |
| 17-β-estradiol | 1.0 | 50 μg |
| Testosterone | 5.0 | 250 μg |
| 2-hydroxypropyl-β-cyclodextrin | 240 | 12 mg |
| benzalkonium chloride | 0.1 | 5 μg |
| EDTA | 1.0 | 50 μg |
| Sorbitol | 61.6 | 3.1 mg |
| water, USP | as required | |

Example 3

Intranasal Administration of Deslorelin to Premenopausal Women with Uterine Leiomyomata A 12 week study was performed to establish an effective dose of deslorelin for controlling heavy bleeding secondary to uterine leiomyomata. Forty-one premenopausal women completed the study and are identified as Subject Nos. 1 through 41. The women were divided into test groups for treatment with intranasal deslorelin as follows:

| Group 1 | Subject Nos. 1–6 | placebo, 0 mg deslorelin |
| Group 2 | Subject Nos. 7–21 | 0.5 mg deslorelin, once per day |
| Group 3 | Subject Nos. 22–34 | 1.0 mg deslorelin, once per day |
| Group 4 | Subject Nos. 35–41 | 2.0 mg deslorelin, once per day |

The intranasal preparation consisted of deslorelin at the indicated concentration along with sorbitol (61.6 mg/mL), benzalkonium chloride (0.1 mg/mL), and water.

The average age of the women was 42.3 years, with similar distribution among groups. For one complete menstrual cycle prior to treatment, each woman completed a daily bleeding calendar. Eligible subjects were then treated with deslorelin at the assigned dosage once per day by intranasal application. During the 12 weeks of daily intranasal administration, each woman kept a daily bleeding calendar, completed quality of life questionnaires, and underwent clinical assessment and laboratory testing. The subjects were tracked for 6 weeks post-treatment for further assessment and to document time to recovery of menses after last drug treatment day. Clinical assessments included grading of nasal irritation (Table 5A), determination of uterine size (Table 5B), and serum hormone levels (Table 5C). The bleeding scores are presented in Table 5D.

TABLE 5A

Nasal Irritation

| | | Number of Study Subjects | | | |
|---|---|---|---|---|---|
| | Deslorelin (mg/day) | 0 mg | 0.5 mg | 1 mg | 2 mg |
| Baseline | None | 11 | 11 | 13 | 9 |
| | Slight | 2 | 3 | 0 | 2 |
| | Moderate | 0 | 0 | 1 | 3 |
| | Quite a bit | 0 | 0 | 0 | 0 |
| | Extreme | 0 | 0 | 0 | 0 |
| | Total | 13 | 14 | 14 | 14 |
| End of Week 4 | None | 13 | 11 | 13 | 12 |
| | Slight | 0 | 2 | 0 | 1 |
| | Moderate | 0 | 1 | 1 | 0 |
| | Quite a bit | 0 | 0 | 0 | 1 |
| | Extreme | 0 | 0 | 0 | 0 |
| | Total | 13 | 14 | 14 | 14 |
| End of Week 8 | None | 13 | 11 | 13 | 11 |
| | Slight | 0 | 1 | 1 | 3 |
| | Moderate | 0 | 1 | 0 | 0 |
| | Quite a bit | 0 | 1 | 0 | 0 |
| | Extreme | 0 | 0 | 0 | 0 |
| | Total | 13 | 14 | 14 | 14 |
| End of Week 12 | None | 13 | 11 | 13 | 8 |
| | Slight | 0 | 2 | 0 | 5 |
| | Moderate | 0 | 0 | 0 | 1 |
| | Quite a bit | 0 | 1 | 1 | 0 |
| | Extreme | 0 | 0 | 0 | 0 |
| | Total | 13 | 14 | 14 | 14 |

TABLE 5B

Uterine Size

| Deslorelin (mg/day) | Mean Difference* |
|---|---|
| 0 mg | +11.6 |
| 0.5 mg | −109.6 |
| 1 mg | −63.6 |
| 2 mg | −246.5 |

*End of week 12 minus baseline uterine volume (cm$^3$)

TABLE 5C

Hormone Levels

| | Estradiol (pg/mL) | Progesterone (ng/dL) | Testosterone (ng/dL) |
|---|---|---|---|
| Baseline | | | |
| 0 mg | 164 | 560 | 32 |
| 0.5 mg | 173 | 641 | 24 |
| 1 mg | 123 | 480 | 26 |
| 2 mg | 184 | 337 | 34 |

TABLE 5C-continued

Hormone Levels

|  | Estradiol (pg/mL) | Progesterone (ng/dL) | Testosterone (ng/dL) |
|---|---|---|---|
| End of Week 4 | | | |
| 0 mg | 141 | 121 | 27 |
| 0.5 mg | 47 | 40 | 19 |
| 1 mg | 51 | 12 | 22 |
| 2 mg | 14 | 12 | 16 |
| End of Week 8 | | | |
| 0 mg | 134 | 142 | 31 |
| 0.5 mg | 79 | 30 | 22 |
| 1 mg | 95 | 25 | 20 |
| 2 mg | 31 | 14 | 20 |
| End of Week 12 | | | |
| 0 mg | 152 | 382 | 29 |
| 0.5 mg | 66 | 37 | 23 |
| 1 mg | 30 | 10 | 16 |
| 2 mg | 30 | 13 | 20 |

TABLE 5D

Bleeding Score*

| | Deslorelin (mg/day) | | | |
|---|---|---|---|---|
| | 0 mg | 0.5 mg | 1 mg | 2 mg |
| Baseline Score | 10.2 | 10.9 | 10.8 | 14.1 |
| Weeks 1–4 | 9.5 | 6.6 | 7.8 | 6.6 |
| Weeks 5–8 | 8.4 | 3.5 | 0.4 | 1.2 |
| Weeks 9–12 | 5.2 | 2.6 | 1.7 | 0.6 |

*Bleeding scores were calculated from the sum of daily diary entries for the 28 day interval prior to the reporting period. No bleeding throughout the interval was a score of 0, 'normal' menstrual flow was a score of 5, and menorrhagia was a score of 10 or greater.

Example 4

Intranasal Administration of GnRH compound, an Estrogen, and an Androgen to Oophorectomized Women Six volunteer women with prior oophorectomies and not presently on hormone replacement therapy were recruited. Each woman was treated with 50 µL of a nasal spray preparation, prepared as described in Example 2, on two occasions separated by one week. The 50 µL dose delivered 1 mg deslorelin, 50 µg 17-β-estradiol, and 250 µg testosterone. Blood samples were collected 20 minutes and 10 minutes prior to dosing on day 1 and on day 8, and then at the following intervals after dosing on each day: 10, 20, 30, 40, 60, 90, 120, 180, 240, 360, and 1440 minutes. Serum estradiol and testosterone levels were determined from the samples, and the baseline corrected cumulative area under the curve from 0 to 360 minutes for each patient for each dose are presented in FIGS. 2A–2B.

Example 5

Intranasal Administration of Deslorelin, Estradiol, and Testosterone to Premenopausal Women Nine premenopausal women, ages 20–45 years, were recruited and randomly divided into three test groups for a 29 day study. The patients in Group 1, Group 2, and Group 3 were treated with the intranasal preparation similar to that described in Example 2 but with deslorelin acetate concentrations of 5 mg/mL (Group 1), 10 mg/mL (Group 2), or 20 mg/mL (Group 3). The single daily intranasal administration consisted of a 100 µL dose delivered using a metered nasal spray device as two 50 µL sprays, one in each nostril.

An indwelling intravenous catheter was inserted in an arm vein for withdrawal of blood samples prior to drug administration and at defined intervals post administration (study day 1) of 40, 120, 240, and 480 minutes. Thereafter, weekly blood samples (study days 8, 15, and 22) were collected for determination of serum estradiol, progesterone, testosterone, and deslorelin levels. On study day 29 post administration, blood samples were drawn according to the same regimen as on study day 1. After collection, all blood samples were allowed to clot at room temperature, then refrigerated. Within 24 hours of collection, serum was separated and stored frozen at −5° C. until assayed.

Serum levels of estradiol, testosterone, and progesterone were quantitated by sensitive and specific radioimmunoassay methods (Stanczyk, F. Z. et al., *Am. J Obstet. Gynecol.*, 159(6):1540 (1988); Scott et al., *Am. J Obstet. Gynecol.*, 130(7):817 (1978)). Prior to assay of the steroid hormones, serum was extracted with ethyl acetate:hexane (1:1) and for the testosterone assay further purified via Celite™ column chromatography, with 40% toluene to elute the testosterone. Procedural losses were followed by addition of 1000 dpm of the appropriate tritiated internal standard. The sensitivities of the estradiol, testosterone, and progesterone assays were 8 pg/mL, 4 ng/dL, and 10 ng/dL, respectively. Assay accuracy was demonstrated by observed parallelism between standard curves and serially diluted serum with respect to each hormone. Intra- and inter-assay coefficients of variation were 5 to 10% and 10 to 15%, respectively. Specificity of the assays was enhanced by eliminating interfering metabolites with extraction and/or chromatography and through the use of highly specific antisera.

The results of all hormone analyses are presented for each subject in Tables 6A through 6C.

TABLE 6A

Hormone Levels for Patients Treated with 0.5 mg/mL Deslorelin

| Study Subject* | Study Day | Time | Estradiol pg/mL | Testosterone ng/dL | Progesterone ng/dL |
|---|---|---|---|---|---|
| #1 | 1 | 0 | 61 | 31 | 110 |
| | | 40 | 91 | 142 | |
| | | 120 | | | |
| | | 240 | | | |
| | | 480 | | | |
| | 8 | | 159 | 29 | 90 |
| | 15 | | 300 | 28 | 100 |
| | 22 | | 10 | 15 | 40 |
| | 29 | 0 | 14 | 13 | 100 |
| | | 40 | 57 | 137 | |
| | | 120 | | | |
| | | 240 | | | |
| | | 480 | | | |
| | 42 | | | | 1260 |
| #2 | 1 | 0 | 33 | 18 | 100 |
| | | 40 | 42 | 43 | |
| | | 120 | | | |
| | | 240 | | | |
| | | 480 | | | |
| | 8 | | 130 | 25 | 50 |
| | 15 | | 160 | 25 | 40 |
| | 22 | | 39 | 19 | 50 |
| | 29 | 0 | 52 | 18 | 60 |
| | | 40 | 50 | 20 | |
| | | 120 | | | |

TABLE 6A-continued

Hormone Levels for Patients Treated with 0.5 mg/mL Deslorelin

| Study Subject* | Study Day | Time | Estradiol pg/mL | Testosterone ng/dL | Progesterone ng/dL |
|---|---|---|---|---|---|
|  |  | 240 |  |  |  |
|  |  | 480 |  |  |  |
|  | 42 |  |  |  | 40 |
| #3 | 1 | 0 | 54 | 21 | 90 |
|  |  | 40 | 128 | 190 |  |
|  |  | 120 |  |  |  |
|  |  | 240 |  |  |  |
|  |  | 480 |  |  |  |
|  | 8 |  | 85 | 39 | 110 |
|  | 15 |  | 98 | 36 |  |
|  | 22 |  | 37 | 22 | 40 |
|  | 29 | 0 | 103 | 86 | 70 |
|  |  | 40 | 112 | 142 |  |
|  |  | 120 |  |  |  |
|  |  | 240 |  |  |  |
|  |  | 480 |  |  |  |
|  | 42 |  |  |  |  |

*Treated with the nasal preparation of Example 2 having 0.5 mg/mL deslorelin acetate.

TABLE 6B

Hormone Levels for Patients Treated with 1.0 mg/mL Deslorelin

| Study Subject* | Study Day | Time | Estradiol pg/mL | Testosterone ng/dL | Progesterone ng/dL |
|---|---|---|---|---|---|
| #4 | 1 | 0 | 73 | 21 | 40 |
|  |  | 40 | 98 | 81 |  |
|  |  | 120 |  |  |  |
|  |  | 240 |  |  |  |
|  |  | 480 |  |  |  |
|  | 8 |  | 167 | 31 | 50 |
|  | 15 |  | 91 | 33 | 50 |
|  | 22 |  | 86 | 24 | 50 |
|  | 29 | 0 | 40 | 23 | 60 |
|  |  | 40 | 126 | 144 |  |
|  |  | 120 |  |  |  |
|  |  | 240 |  |  |  |
|  |  | 480 |  |  |  |
|  | 42 |  |  |  |  |
| #5 | 1 | 0 | 73 | 21 | 220 |
|  |  | 40 | 227 | 250 |  |
|  |  | 120 |  |  |  |
|  |  | 240 |  |  |  |
|  |  | 480 |  |  |  |
|  | 8 |  | 26 | 19 | 50 |
|  | 15 |  | 27 | 23 | 30 |
|  | 22 |  | 132 | 37 | 50 |
|  | 29 | 0 | 45 | 25 | 40 |
|  |  | 40 | 98 | 102 |  |
|  |  | 120 |  |  |  |
|  |  | 240 |  |  |  |
|  |  | 480 |  |  |  |
|  | 42 |  |  |  |  |
| #6 | 1 | 0 | 51 | 20 | 60 |
|  |  | 40 | 181 | 174 |  |
|  |  | 120 |  |  |  |
|  |  | 240 |  |  |  |
|  |  | 480 |  |  |  |
|  | 8 |  | 45 | 26 | 80 |
|  | 15 |  | 18 | 20 | 70 |
|  | 22 |  | 48 | 16 | 60 |
|  | 29 | 0 | 29 | 20 | 100 |
|  |  | 40 | 89 | 98 |  |
|  |  | 120 |  |  |  |
|  |  | 240 |  |  |  |
|  |  | 480 |  |  |  |
|  | 42 |  |  |  |  |

*Treated with the nasal preparation of Example 2 having 1.0 mg/mL deslorelin acetate.

TABLE 6C

Hormone Levels for Patients Treated with 2.0 mg/mL Deslorelin

| Study Subject* | Study Day | Time | Estradiol pg/mL | Testosterone ng/dL | Progesterone ng/dL |
|---|---|---|---|---|---|
| #7 | 1 | 0 | 32 | 14 | 90 |
|  |  | 40 | 141 | 149 |  |
|  |  | 120 |  |  |  |
|  |  | 240 |  |  |  |
|  |  | 480 |  |  |  |
|  | 8 |  | 21 | 13 | 50 |
|  | 15 |  | 16 | 14 | 60 |
|  | 22 |  | 12 | 9 | 40 |
|  | 29 | 0 | 23 | 10 | 70 |
|  |  | 40 | 40 | 24 |  |
|  |  | 120 |  |  |  |
|  |  | 240 |  |  |  |
|  |  | 480 |  |  |  |
|  | 42 |  |  |  |  |
| #8 | 1 | 0 | 61 | 15 | 80 |
|  |  | 40 | 191 | 244 |  |
|  |  | 120 |  |  |  |
|  |  | 240 |  |  |  |
|  |  | 480 |  |  |  |
|  | 8 |  | 149 | 30 | 50 |
|  | 15 |  | 302 | 39 | 70 |
|  | 22 |  | 22 | 22 | 150 |
|  | 29 | 0 | 90 | 25 | 70 |
|  |  | 40 | 117 | 88 |  |
|  |  | 120 |  |  |  |
|  |  | 240 |  |  |  |
|  |  | 480 |  |  |  |
|  | 42 |  |  |  |  |
| #9 | 1 | 0 | 37 | 21 | 30 |
|  |  | 40 | 152 | 241 |  |
|  |  | 120 |  |  |  |
|  |  | 240 |  |  |  |
|  |  | 480 |  |  |  |
|  | 8 |  | 158 | 110 | 20 |
|  | 15 |  | 18 | 18 | 20 |
|  | 22 |  | 24 | 15 | 10 |
|  | 29 | 0 | 29 | 14 | 20 |
|  |  | 40 | 143 | 132 |  |
|  |  | 120 |  |  |  |
|  |  | 240 |  |  |  |
|  |  | 480 |  |  |  |
|  | 42 |  |  |  |  |

*Treated with the nasal preparation of Example 2 having 2.0 mg/mL deslorelin acetate.

Example 6

Comparison of Intranasally and Transdermally Delivered Estradiol

Naturally postmenopausal or surgically postmenopausal females (n=63) were recruited for the study. Thirty women were selected for treatment with transdermal estradiol from a Noven Vivelle® 50 µg/day patch. Thirty women were treated with transdermal estradiol from a Noven Vivelle-dote® 50 µg/day patch. The remaining three women were treated with a single bolus, 100 µL volume, nasal spray containing 350 µg 17-β-estradiol per 100 µL bolus. The nasal formulation in addition to estradiol was comprised of sorbitol (61.6 mg/mL), EDTA (1.0 mg/mL), benzalkonium chloride (0.1 mg/mL), and 2-hydroxypropyl-β-cyclodextrin (100 mg/mL).

Blood samples were drawn at defined intervals for analysis of serum estradiol levels. The average concentration over 24 hours as pg/mL was determined and the results are shown in Table 7.

TABLE 7

Average Estradiol Concentration Over 24 Hours (pg/mL) after Treatment with Transdermal and Intranasal Estradiol

| Estradiol Dosage Form | Average Concentration over 24 Hours (pg/mL) |
|---|---|
| transdermal, Vivelle ® 50 µg/day patch | 34.4 |
| transdermal, Vivelle-dot ® 50 µg/day patch | 36.8 |
| intranasal, 350 µg/spray | 37.8 |

Example 7

Intranasal Delivery of GnRH Compound with Transdermal or Intranasal Co-administration of Estradiol Women with endometriosis treated with intranasal deslorelin (GnRH compound) were assigned to one of three methods of add-back: 1) 50 µg/day estradiol transdermal patch, 2) 300 µg/day intranasal estradiol, or 3) 300 µg/day intranasal estradiol with 275 µg/day intranasal testosterone. Treatment efficacy was measured by evaluating the decrease in endometriosis symptoms associated with treatment. Evaluated were symptoms and signs of endometriosis using a standard scoring system that takes into account 3 symptoms (pelvic pain, dysmenorrhea, and dyspareunia) and two signs (pelvic tenderness and pelvic induration). The composite score physical symptoms and signs score (CPSSS) is the sum of the scores for each individual symptom or sign (0 to 3 with 0 being not present and 3 being the most severe). Shown in Table 8A is the change in CPSSS following 3 and 6 months of treatment.

TABLE 8A

CPSSS after 3 and 6 Months of Drug Treatment

| | Baseline CPSSS | Month 3 | Month 6 | No. of subjects |
|---|---|---|---|---|
| Deslorelin + Transdermal Estradiol | 7.4 | 4.0 | 3.8 | 5 |
| Deslorelin + Intranasal Estradiol | 8.1 | 2.3 | 3.4 | 7 |
| Deslorelin + Intranasal Estradiol + Testosterone | 6.8 | 1.6 | 3.1 | 8 |

Bone mineral density (BMD) of the lumbar spine was obtained by dual-energy X-ray absorptiometry (DEXA) prior to and after six months of drug treatment. BMD changes are shown in Table 8B as the ratio of the 6 month value compared to the baseline value. BMD of subjects treated with deslorelin alone (Example 8) was 0.971 of the baseline value.

TABLE 8B

Effect of Add-back Estradiol on the Ratio of 6 Month BMD to BaselineBMD

| | Mean Ratio ($BMD_{6\ mo}/BMD_{baseline}$) | No. of subjects |
|---|---|---|
| Deslorelin* | 0.971 | 36 |
| Deslorelin + Transdermal Estradiol | 0 978 | 5 |
| Deslorelin + Intranasal Estradiol | 0.996 | 7 |
| Deslorelin + Intranasal Estradiol + Testosterone | 0.999 | 8 |

*From study described in Example 8.

Example 8

Intranasal Delivery of GnRH Compound with Transdermal Co-Administration of Estradiol Example 8 describes an intranasally delivered GnRH compound with co-administration of estradiol. Premenopausal females (n=265) with uterine fibroids were recruited for participation in a 12 month double blind study. The women were randomly assigned to treatment in one of the following five study arms:

| Arm 1 | placebo/placebo |
|---|---|
| Arm 2 | deslorelin, intranasal/placebo for 6 months; then crossed over to arm 5 |
| Arm 3 | deslorelin, intranasal/25 µg estradiol, transdermal |
| Arm 4 | deslorelin, intranasal/50 µg estradiol, transdermal |
| Arm 5 | deslorelin, intranasal/75 µg estradiol, transdermal |

Deslorelin at a daily dose of 1 mg was administered intranasally using a conventional metered spray delivery device. The intranasal preparation was a 100 µL daily nasal spray containing 1.0 mg deslorelin. Estradiol was administered transdermally using a commercially available twice-weekly patch that delivered either 25 µg estradiol or 50 µg estradiol per day. Subjects in Arm 5 wore two patches, one at each dosage, to achieve the 75 µg dose.

Women with uterine fibroids often experience very heavy bleeding (menorrhagia) and uterine enlargement leading to pelvic pain and pressure symptoms. Clinical benefit was assessed by measuring changes in bleeding score (percent of subjects with reduction of bleeding into the normal range) and uterine volume. Shown in Table 9A are the percent of subjects responding (reduction of bleeding into the normal range) after 3 and 6 months of treatment. The percent of subjects having a response is significantly greater in the active treatment groups compared to the placebo group. Table 9B shows the change in uterine volume (expressed as proportion of initial volume) associated with treatment. The placebo group had an increase in uterine volume and active treatment resulted in decreased uterine volume.

TABLE 9A

Percent of Subjects with Reduction of Bleeding into the Normal Range

| | 3 Months | | 6 Months | |
|---|---|---|---|---|
| | No. of Subjects | % with reduction | No. of subjects | % with reduction |
| Placebo | 79 | 10 | 70 | 17 |
| Deslorelin | 36 | 69 | 36 | 92 |
| Deslorelin + 25 µg/day transdermal estradiol | 32 | 75 | 27 | 85 |
| Deslorelin + 50 µg/day transdermal estradiol | 37 | 73 | 35 | 66 |
| Deslorelin + 75 µg/day transdermal estradiol | 42 | 81 | 38 | 68 |

TABLE 9B

Proportion of Uterine Volume: Volume after 6 Months of Treatment Compared to Baseline

|  | 6 Months | |
|---|---|---|
|  | No. of subjects | Proportion of Initial Volume |
| Placebo | 60 | 1.238 |
| Deslorelin | 33 | 0.675 |
| Deslorelin + 25 µg/day transdermal estradiol | 24 | 0.805 |
| Deslorelin + 50 µg/day transdermal estradiol | 31 | 0.789 |
| Deslorelin + 75 µg/day transdermal estradiol | 37 | 0.910 |

Safety was assessed by examining endometrial tissue for evidence of hyperplasia. At the end of the 12 month treatment period an endometrial biopsy was taken for analysis of the endometrial morphology. The results are shown in Table 9C.

TABLE 9C

Incidence of Simple Hyperplasia from Endometrial Biopsy

|  | Arm | | | | | |
|---|---|---|---|---|---|---|
|  | 1 | 2 | 3 | 4 | 5 | 4&5 |
| No of subjects with simple hyperplasia | 1 | 2 | 0 | 1 | 0 | 1 |
| Total no of subjects studied | 45 | 12 | 6 | 24 | 25 | 49 |
| Proportion of subjects with simple hyperplasia | 0.022 | 0.167 | 0.000 | 0.042 | 0.000 | 0.020 |

Example 9

Intranasal Delivery of GnRH Compound with Co-administration of Transdermal or Intranasal Estradiol±Testosterone Twenty premenopausal women with endometriosis were recruited and randomly assigned for treatment as follows:

| Arm 1 | deslorelin, intranasal/ estradiol, transdermal | n = 5 |
| Arm 2 | deslorelin, and estradiol, intranasal | n = 7 |
| Arm 3 | deslorelin, estradiol, and testosterone, intranasal | n = 8 |

The Arm 1 intranasal formulation contained 1 mg deslorelin; estradiol was delivered transdermally from a twice-weekly commercially-available 50 µg/day estradiol patch. The intranasal formulations used in Arms 2 and 3 contained 1 mg deslorelin and 300 µg estradiol (Arm 2), and additionally 275 µg testosterone (Arm 3), formulated in a similar manner as that described in Example 2.

After the six month treatment period the incidence of endometrial hyperplasia was evaluated by biopsy in 20 subjects. The results are shown in Table 10.

TABLE 10

|  | Endometrial Response | | | | |
|---|---|---|---|---|---|
|  | Hyperplasia | Proliferative | Atrophic | Insufficient Tissue | Refused |
| Baseline | 0 | 17 | 0 | 3 | 0 |
| Month 6 | 0 | 16 | 0 | 3 | 1 |

Although the invention has been described with respect to particular embodiments, it will be apparent to those skilled in the art that various changes and modifications can be made without departing from the invention.

It is claimed:

1. A nasal spray formulation, consisting essentially of an aqueous medium having dissolved therein
   (i) a GnRH compound, and
   (ii) an estrogenic compound, and optionally an androgenic compound, present in the form of a water-soluble complex with a water-soluble cyclodextrin
   where the concentration of GnRH compound and estrogenic compound in the formulation are effective, when administered intranasally, to suppress ovarian estrogen and progesterone production and to prevent signs and symptoms of estrogen deficiency, without a significant increase in the risk of endometrial hyperplasia.

2. The formulation of claim 1, wherein the cyclodextrin is 2-hydroxypropyl-β-cyclodextrin, at a concentration between 50 and 300 mg/mL.

3. The formulation of claim 2, wherein the 2-hydroxypropyl-β-cyclodextrin has a degree of substitution between 2 and 8.

4. The formulation of claim 1, wherein the GnRH compound is deslorelin, at a daily dose between 0.025 and 1.5 mg.

5. The formulation of claim 1, wherein the estrogenic compound is 17-β-estradiol, at a daily dose between 0.15 and 0.6 mg.

6. The formulation of claim 5, which further includes testosterone in the form of a water-soluble complex with the cyclodextrin, and at a daily dose of between 0.15 and 1 mg.

7. The formulation of claim 6, wherein the estrogenic compound and testosterone have a combined molar occupancy with respect to the cyclodextrin that is greater than the molar occupancy achievable with either steroid alone.

8. The formulation of claim 7, wherein the cyclodextrin is 2-hydroxypropyl-β-cyclodextrin having a degree of substitution between 2 and 8, and a concentration between 50 and 300 mg/mL.

9. The formulation of claim 1, wherein the GnRH compound is a GnRH peptide agonist.

10. The formulation of claim 1, wherein the GnRH compound is selected from the group consisting of deslorelin, leuprolide, nafarelin, goserelin, decapeptyl, buserelin, histrelin, gonadorelin, abarelix, cetrorelix, azaline B, and degarelix, and analogs thereof.

11. A nasal spray formulation, consisting essentially of an aqueous medium having dissolved therein (i) a GnRH compound, and (ii) an estrogenic compound, and optionally an androgenic compound, present in the form of a water-soluble complex with a water-soluble cyclodextrin wherein said formulation when intranasally administered as a daily bolus (i) is effective to achieve an average serum concentration over 24 hours of the estrogenic compound that is within 10% of the average serum concentration over 24 hours of the estrogenic compound when delivered transdermally and (ii) is as effective in preventing bone mineral density loss as transdermal administration of the estrogenic compound.

12. The formulation of claim 11, wherein the cyclodextrin is 2-hydroxypropyl-β-cyclodextrin.

13. The formulation of claim 11, wherein the GnRH compound is a GnRH peptide agonist.

14. The formulation of claim 11, wherein the GnRH compound is selected from the group consisting of deslorelin, leuprolide, nafarelin, goserelin, decapeptyl, buserelin, histrelin, gonadorelin, abarelix, cetrorelix, azaline B, and degarelix, and analogs thereof.

15. The formulation of claim 11, wherein the GnRH compound is deslorelin, at a daily dose between 0.025 and 1.5 mg.

16. The formulation of claim 11, wherein the estrogenic compound is 17-β-estradiol, at a daily dose between 0.15 and 0.6 mg.

17. The formulation of claim 11, which further includes testosterone in the form of a water-soluble complex with the cyclodextrin, and at a daily dose of between 0.15 and 1 mg.

18. The formulation of claim 17, wherein the estrogenic compound and the testosterone have a combined molar occupancy with respect to the cyclodextrin that is greater than the molar occupancy achievable with either steroid alone.

* * * * *